United States Patent
Dixon

(10) Patent No.: US 8,269,192 B2
(45) Date of Patent: Sep. 18, 2012

(54) METHOD AND APPARATUS FOR DETERMINING THE PRESENCE OF OPTICAL BRIGHTENERS IN WATER SAMPLES

(75) Inventor: Laura Kellie Dixon, Bradenton, FL (US)

(73) Assignee: Mote Marine Laboratory, Inc., Sarasota, FL (US)

( * ) Notice: Subject to any disclaimer, the term of this patent is extended or adjusted under 35 U.S.C. 154(b) by 273 days.

(21) Appl. No.: 12/698,424

(22) Filed: Feb. 2, 2010

(65) Prior Publication Data

US 2011/0186753 A1 Aug. 4, 2011

(51) Int. Cl.
*G01N 21/64* (2006.01)
(52) U.S. Cl. .................. 250/459.1; 250/373; 250/458.1; 250/461.1
(58) Field of Classification Search .................. 250/373, 250/458.1, 459.1, 461.1
See application file for complete search history.

(56) References Cited

U.S. PATENT DOCUMENTS

| | | | |
|---|---|---|---|
| 4,112,741 A | 9/1978 | Kerfoot et al. | |
| 4,686,372 A | 8/1987 | Satoru et al. | |
| 5,700,370 A | 12/1997 | Helmo | |
| 7,132,254 B2 | 11/2006 | Vincent | |

OTHER PUBLICATIONS

Hartel et al., Combining targeted sampling and fluorometry to identify human fecal contamination in a freshwater creek, 2008, Journal of Water and Health, pp. 105-116.*

Cioffi et al., Fluorescent Whitening Agents as Facile Anthropogenic Pollution Indicators in Estuarine and Surface Waters, Aug. 1999, pp. 1-7.*
Anastasiou C.J., "*Optical Brightener Detection for Tracking Wastewater Contributions to Coastal, Estuarine, and Freshwater Systems, Task 2 Summary Report*", 39 pp (Aug. 2007).
Bricaud A, et al., "*Absorption by dissolved organic matter of the sea (yellow substance) in the UV and visible domains*", Limnology & Oceanography 26 (1):43-53 (1981).
Dixon L.K. and Julian P., "*Phillippi Creek Optical Brightener Investigation for Sarasota County Water Resources*", Mote Marine Laboratory, Technical Report No. 1038, 48 pp, (Aug. 31, 2005).
Dixon, L.K. et al., "*Development of a fluorescent method to detect optical brighteners in the presence of varying concentrations of fluorescent humic substances: Identifying regions influenced by OSTDS in the estuarine waters of Charlotte Harbor*", Mote Marine Laboratory Technical Report No. 1045 (Sep. 19, 2005).
Dixon, L. and Buehler, C., "*Evaluation of EEM Methodology for Detection of OSTDS Effluent in Ambient Surface Waters*", Mote Marine Laboratory, Technical Report No. 1186, 84 pp (Jun. 22, 2007).

(Continued)

*Primary Examiner* — Christine Sung
(74) *Attorney, Agent, or Firm* — IPLM Group, P.A.

(57) ABSTRACT

An apparatus and method for making quantitative measurements of the amounts of optical brighteners in water samples using fluorescence measurements at multiple wavelengths. First and second emission wavelength raw measurements are corrected for sample absorption to provide absorption-corrected first emission wavelength and second emission wavelength fluorescence emission values. The absorption-corrected first emission wavelength value is compared to the absorption-corrected second emission wavelength value and to similarly-determined and similarly absorption-corrected emission wavelength values or a ratio thereof obtained from a comparison water sample in which optical brighteners are not present or are only minimally present, to provide a quantitative optical brightener measurement. The apparatus and method may be field-based or laboratory-based, and may operate on a flow-through basis or on discrete samples.

20 Claims, 4 Drawing Sheets

OTHER PUBLICATIONS

Dixon, L. and Buehler, C., "*Evaluation of EEM Methodology for Detection of OSTDS Effluent in Ambient Surface Waters: Final Report*", Mote Marine Laboratory, Technical Report No. 1205, 91pp (Sep. 5, 2007).

Hagedorn, Charles et al., "*Fluorometric Detection of Optical Brighteners as an Indicator of Human Sources of Water Pollution. Part I: Description and Detection of Optical Brighteners*", Crop and Soil, Environmental News, 7 pp, Nov. 2005, downloadable from http://filebox.vt.edu/users/chagedor/biol_4684/BST/OB%20Article-I.pdf.

Hagedorn, Charles et al., "*Fluorometric Detection of Optical Brighteners as an Indicator of Human Sources of Water Pollution. Part II: Development as a Source Tracking Methodology in Open Waters*", Crop and Soil, Environmental News, 14 pp, Nov. 2005, downloadable from http://filebox.vt.edu/users/chagedor/biol_4684/BST/OB%20Article-II.pdf.

Hartel P.G. et al., "Exposing water samples to ultraviolet light improves fluorometry for detecting human fecal contamination", SCCWRP Annual Report, pp. 281-298 (2007).

Jerlov, N.G., "*Marine Optics*", Elsevier Oceanography Series, 14, Cover Page, Table of Contents and Chapter 3, 27 pp (1976).

Lakowicz, J.R., "*Principles of Fluorescence Spectroscopy, $3^{rd}$ Edition*", Center for Fluorescence Spectroscopy, University of Maryland School of Medicine, 21 pp, (2006).

Mopper, K., et al., "*Photochemical degradation of dissolved organic carbon and its impact on the oceanic carbon cycle*", Nature vol. 353: 60-62 (Sep. 5, 1991).

Moran, M.A. et al., "*Role of photoreaction in the formation of biologically labile compounds from dissolved organic matter*", Limnology and Oceanography, vol. 42(6):1307-1316 (Sep. 1997).

Dixon, L.K., "*Optical Brighteners: PARAFAC analyses of EEM fluorescence data for the conceptual design of field instrumentation and methods, Final Report*", Mote Marine Laboratory, Technical Report No. 1316, 64 pp, (Feb. 16, 2009).

Waye, D., "*Detecting Sewage Leaks with Optical Brightener Monitoring*", The Volunteer Monitor 15:16-17 (Summer 2003).

\* cited by examiner

METHOD AND APPARATUS FOR DETERMINING THE PRESENCE OF OPTICAL BRIGHTENERS IN WATER SAMPLES

STATEMENT REGARDING FEDERALLY SPONSORED RESEARCH OR DEVELOPMENT

Work related to this invention was funded by Clean Water Act §104(b)(3) Gulf of Mexico Program Grant No. MX96423005-4 from the U.S. Environmental Protection Agency ("EPA"), under a contract between the EPA and the Southwest District of the Florida Department of Environmental Protection.

TECHNICAL FIELD

The present invention relates to water analysis.

BACKGROUND

Septic tank systems, also referred to as on-site sewage treatment and disposal systems (OSTDS), are frequently used for wastewater treatment and disposal. When properly designed, installed and maintained, an OSTDS can be effective in removing organic matter, bacteria and nutrients from wastewater. However, certain conditions, such as proximity to surface waters, unsuitable soils, high water tables or improper maintenance or use can interfere with or prevent proper functioning of an OSTDS. When such conditions exist, the level of treatment may be insufficient to protect water quality in nearby receiving bodies of water. Wastewater effluents, although meeting all permitted water quality criteria, can also result in deleterious water quality effects.

Many conventional sampling methods for assessing wastewater contamination rely on determining concentrations of fecal coliform bacteria. Although high concentrations of fecal coliform bacteria are found in human sewage, numerous non-human sources of fecal coliform are present in urbanized watersheds, with many animals producing far greater daily fecal coliform counts than humans. Other water quality parameters often used to test for the presence of septic effluents (e.g., total organic carbon, total nitrogen, total phosphorous, or the ratio of fecal coliform to fecal streptococcus colonies) also have non-anthropogenic sources. As a result, the presence of fecal coliform bacteria or elevated levels of other parameters may not necessarily confirm the presence of domestic waste.

Optical brightener (OB) dyes are brightening agents which are currently added to most laundry detergents sold in the U.S. When exposed to certain wavelengths of ultraviolet (UV) light, OBs fluoresce in the visible region of the spectrum, making materials appear brighter. Water samples that similarly fluoresce when exposed to the same wavelengths of UV light are likely to contain detergent OBs. A variety of OB compounds are employed in laundry detergent formulations, in varying amounts. Because there are no natural sources for OBs, and because laundry effluent is a major component of both septic effluent and domestic wastes treated by OSTDS, OBs are very useful indicators of human waste in surface waters. The presence of OBs in water samples is highly indicative of contamination by sources of human pollution and generally indicates a relatively direct connection between an OSTDS, or some other waste treatment stream, and surface waters. The sensitivity and rapidity of fluorescence techniques make OB detection a cost-effective and useful surrogate for detecting human wastes.

Other substances in surface waters also fluoresce and can interfere with fluorescent OB detection. Natural fluorescent compounds are often present, particularly in freshwater originating as surface drainage from wetlands. Soluble organic components from soils and decomposing plant matter can give a tea- or coffee-color to bodies of water. The soluble organics may collectively be classified as humic acids, fulvic acids or tannins, and more generally may be termed colored, or chromophoric, dissolved organic matter (CDOM). Natural CDOM components are present in constantly changing concentration gradients in estuarine waterways, rivers, streams, lakes and other bodies of water. CDOM components fluoresce under UV light and can interfere with measurements designed to detect OBs.

Although both OB compounds and CDOM components fluoresce under UV light, each has specific and characteristic fluorescence signatures. OBs fluoresce when exposed to UV light at an optimal excitation wavelength in the very near-UV (300-400 nm) range, and exhibit emission wavelengths in the 400-480 nm range, with peak emission wavelengths near 440-450 nm. CDOMs, on the other hand, are a mixture of many different compounds and consequently their emission spectrum is much broader than that of optical brighteners. When exposed to similar UV light, CDOM components fluoresce over the entire range of wavelengths between 350-600 nm, and even beyond at wavelengths longer than 600 nm, resulting in a very broad signal spanning the entire wavelength range from 350 to 600 nm.

SUMMARY OF THE INVENTION

Due to varying CDOM levels, especially in estuaries, streams, rivers, lakes, and other water bodies where a gradient of naturally occurring CDOM may be observed, it is difficult to make rapid quantitative measurements of OB levels, especially while in the field. Field screening or analytical methods for accurately determining the quantity of OBs desirably should separate signals generated by OBs from signals generated by potentially varying CDOM. Within a given geographic region, water samples that contain only CDOM components but no OB compounds produce relatively constant proportional fluorescent signals at wavelengths of 440 nm ($F_{440}$) and 550 nm ($F_{550}$), although the amplitude of both signals varies with CDOM concentration. The ratio of fluorescent signals at these two wavelengths, $F_{440}/F_{550}$, is relatively constant regardless of the amount of CDOM present. Since OBs fluoresce with a strong signal and a comparatively narrow peak, primarily at 440 nm, the presence of OBs in a water sample will result in a higher fluorescence signal at 440 nm than can be expected if only CDOM components are present. Fluorescence at 550 nm is essentially unchanged by the presence of OB. The fluorescence signal at 550 nm can thus be used to predict or estimate the quantitative contribution of fluorescence due to CDOM components to the total fluorescence measured at 440 nm and thereby enable rapid quantitative measurement of the amount of OBs present in a sample.

In addition to fluorescence signals produced by CDOM, a complicating factor when measuring fluorescence in ambient waters is interference by the absorptive properties of CDOM. Due to varying natural CDOM concentrations in waterways, it is desirable to individually or continuously correct raw fluorescence measurements for such absorption in order to provide an accurate measurement of fluorescence. In a sample with high absorptive properties, the excitation light passing through the sample is substantially reduced, leading to reduced fluorescence emission. Subsequently, the emitted light is also further reduced by absorption. If absorption due to CDOM is not corrected for, reduced amplitude of the fluorescence signal will be observed. The reduction in fluorescence is proportional to the amount of CDOM present in a sample and is particularly important when sampling across saline-freshwater gradients or under other conditions of varying CDOM concentrations. With absorption correction included, the linear range of fluorescence response to fluorophore concentration is substantially extended. Including absorption corrections minimizes sample dilution requirements, improves signal to noise ratios, allows analysis of more concentrated samples, and is particularly important when conducting field surveys where dilution of samples is not desirable or where the CDOM concentrations are highly variable. The absorption correction is designed to account for the reduction of excitation energy reaching the sample due to absorption, the consequently reduced fluorescence, and the subsequent reduction in fluorescence emission due to the absorption of sample fluorescence.

The present invention provides, in one aspect, an apparatus for quantitatively measuring the amount of optical brighteners in a selected water sample, the apparatus comprising:

a. a chamber where the selected sample is exposed to ultraviolet excitation at a wavelength of about 300 to 400 nm;
b. one or more fluorometers that measure raw fluorescence emission from such selected sample at a first emission wavelength of about 400 to 500 nm and at a second emission wavelength of about 500 to 600 nm;
c. one or more electronic computational devices that:
   i. correct the first emission wavelength and second emission wavelength raw measurements for sample absorption using measured, modeled or both measured and modeled absorption coefficients to provide absorption-corrected first emission wavelength and second emission wavelength fluorescence emission values;
   ii. compare the absorption-corrected first emission wavelength value to the absorption-corrected second emission wavelength value and to similarly-determined and similarly absorption-corrected emission wavelength values or a ratio thereof obtained from a comparison water sample in which optical brighteners are not present or are only minimally present; and
   iii. determine the amount of optical brighteners in the selected sample.

The present invention provides, in another aspect, a method for quantitative measurement of the amount of optical brighteners in a selected water sample, which method comprises:

a. exposing such selected sample to ultraviolet excitation at a wavelength of about 300 to 400 nm;
b. measuring raw fluorescence emission from such selected sample at a first emission wavelength of about 400 to 500 nm and at a second emission wavelength of about 500 to 600 nm;
c. correcting the first emission wavelength and second emission wavelength raw measurements for sample absorption using measured, modeled or both measured and modeled absorption coefficients to provide absorption-corrected first emission wavelength and second emission wavelength fluorescence emission values;
d. comparing the absorption-corrected first emission wavelength value to the absorption-corrected second emission wavelength value and to similarly-determined and similarly absorption-corrected emission wavelength values or a ratio thereof obtained from a comparison water sample in which optical brighteners are not present or are only minimally present, to determine the amount of optical brighteners in the selected sample.

The disclosed apparatus and method provide field survey (e.g., while on a waterway) and laboratory-based analytical capabilities which may be used for rapid quantitative assessment of the presence of OBs in water samples. The apparatus and method may be used for rapid and inexpensive field screening to identify problematic regions and to enable targeted collection of samples to be subjected to more expensive analytical procedures and more detailed review. The apparatus and method may also be used for rapidly assessing or estimating the extent to which OSTDS or other waste effluent may be responsible for suspected adverse impacts. The apparatus and method enable rapid and accurate separation of fluorescence signals produced by OBs from varying fluorescence signals produced by CDOM, and are particularly advantageous for use in estuarine areas in which a gradient of naturally occurring CDOM may be likely.

DETAILED DESCRIPTION

The disclosed apparatus and method may employ a field-based flow-through fluorometry embodiment or a field-based or laboratory-based embodiment employing discrete collected water samples. Both embodiments may be used for determining OB concentrations or OB and CDOM concentrations in waterways, especially in waters having unknown or varying CDOM concentrations. The discussion that follows will focus on the field-based flow-through fluorometry embodiment, it being understood that the other disclosed embodiments may be made through easily accomplished modifications to the field-based flow-through fluorometry embodiment.

Figure 1:
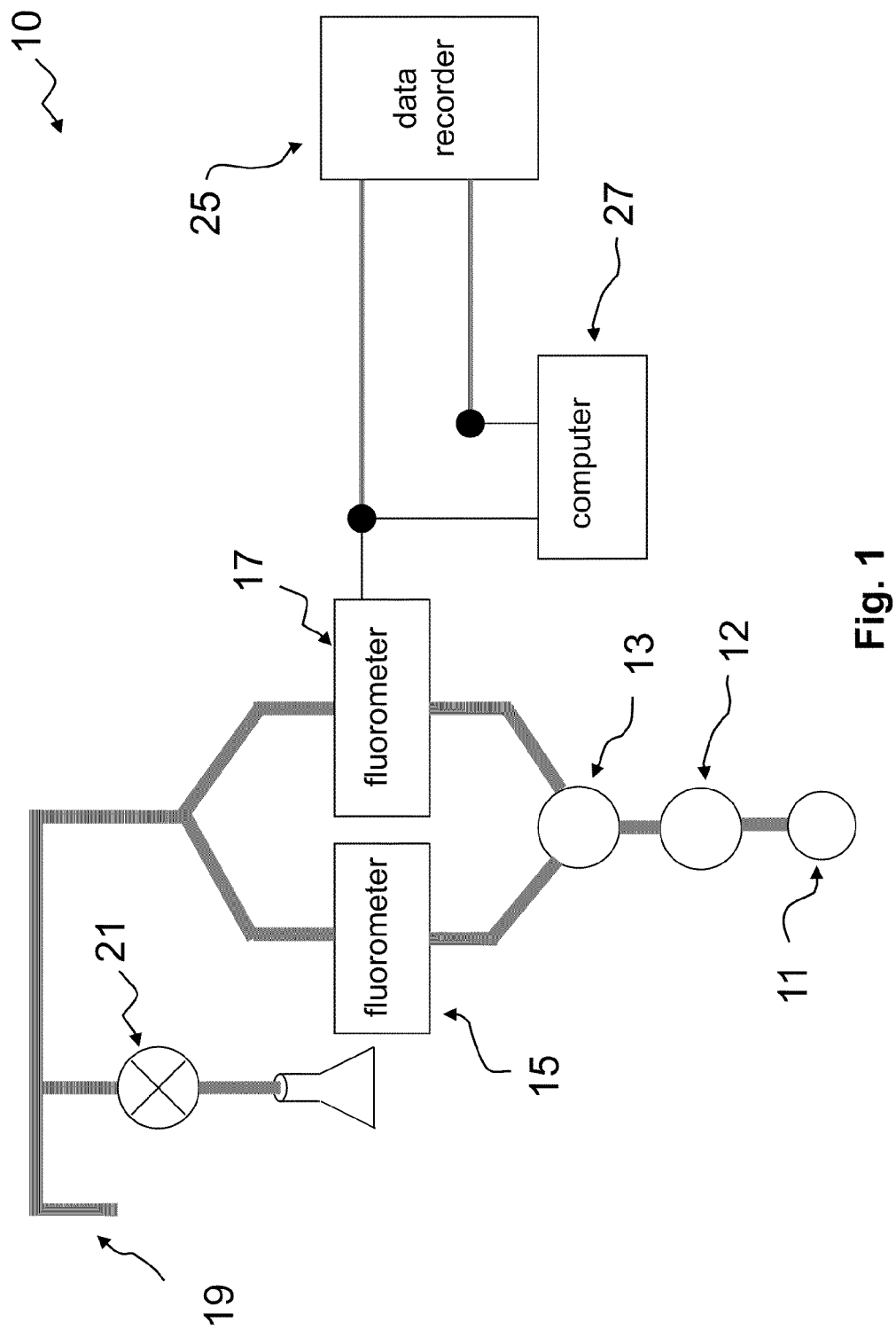
FIG. 1 is a schematic block diagram of a multiple wavelength optical brightener measurement apparatus according to the present invention.

Referring to FIG. 1, apparatus 10 may be transported in a suitable vessel (e.g., a small boat) through waters in which it is desired to determine the amount of OBs originating from OSTDS effluents or other waste streams. A sample intake 11 equipped with a suitable pre-filter (e.g., a 200 mesh filter) and made of a suitable inert material (e.g., PVC or polyethylene tubing) is held beneath the water surface at a pre-selected depth. The pre-filter prevents foreign objects and debris from entering the apparatus. Ambient water is pulled upward through pump 12 and Y-connector 13 for simultaneous delivery to two single channel fluorometers 15 and 17 and measurement of first and second raw emission wavelength data, then discharged overboard at outlet 19. Pump 12 may for example be a submerged or unsubmerged pump, and may operate using direct lift, positive displacement, velocity, buoyancy or gravity (e.g., siphon) operating principles. A sampling valve 21 may be included in the outlet line so that discrete samples may be collected at desired intervals. Collection of such discrete samples enables subsequent and more detailed chemical analysis upon return from the field. In the embodiment shown in FIG. 1, fluorometers 15 and 17 are arranged in a parallel flow circuit to measure raw fluorescence emission at the first and second emission wavelengths. Other arrangements may be used. For example, fluorometers 15 and 17 may be arranged in a series flow circuit to carry out such measurements, or a single fluorometers may if desired be used to measure fluorescence emission at two or more wavelengths. Fluorometers 15 and 17 include chambers in which the selected sample is exposed to ultraviolet excitation at a wavelength of about 300 to 400 nm, and are equipped with filters or other suitable devices to enable fluorescence measurement in the recited first and second emission wavelengths. For example, fluorometers 15 and 17 may respectively include 440 nm and 550 nm filters whose transmission bandwidths are approximately 10 nm wide at one-half the maximum transmission (10 nm FWHM). Variations in wavelength from these preferred values may be employed to produce generally comparable results. In the embodiment shown in FIG. 1, each fluorometer 15 and 17 preferably provides a continuous signal which varies as a function of the fluorescence of the water sample at the selected excitation and measurement wavelengths. A variety of such wavelengths may be employed. In one exemplary embodiment, both fluorometers 15 and 17 are exposed to ultraviolet excitation at a wavelength of 300 to 400 nm, fluorometer 15 measures fluorescence at a wavelength of about 400 to 500 nm (e.g., in a 10 nm range centered on 440 nm to measure fluorescence of both OBs and CDOM) and fluorometer 17 measures fluorescence at a wavelength of about 500 to 600 nm (e.g., in a 10 nm range centered on 550 nm for measuring CDOM alone). Suitable fluorometers are available from a variety of sources including Turner Designs (Sunnyvale, Calif.) and WET Labs (Philomath, Oreg.).

During water sample collection, whether via flow-through fluorometry or via operation of valve 21, the geographic coordinates may be logged at pre-defined intervals, e.g, every 15 sec, using a Global Positioning System (GPS) or other locating apparatus. Continuous raw fluorescence data may be collected using data recorder 25 and may be manipulated (e.g., to correct for absorption or to determine quantitative OB and CDOM levels as discussed in more detail below) and if desired stored or displayed using an electronic computational device such as computer 27. The computer may for example calculate and store or display (or both store and display) real-time OB concentrations using stored or modeled absorption data, absorption correction factors, fluorescence measurement results and if desired stored standardization results or other data as discussed in more detail below. For example, the display may provide quantitative optical brightener information corrected for sample absorption and chromophoric dissolved organic matter levels, and if desired may also provide quantitative chromophoric dissolved organic matter information.

Figure 2:
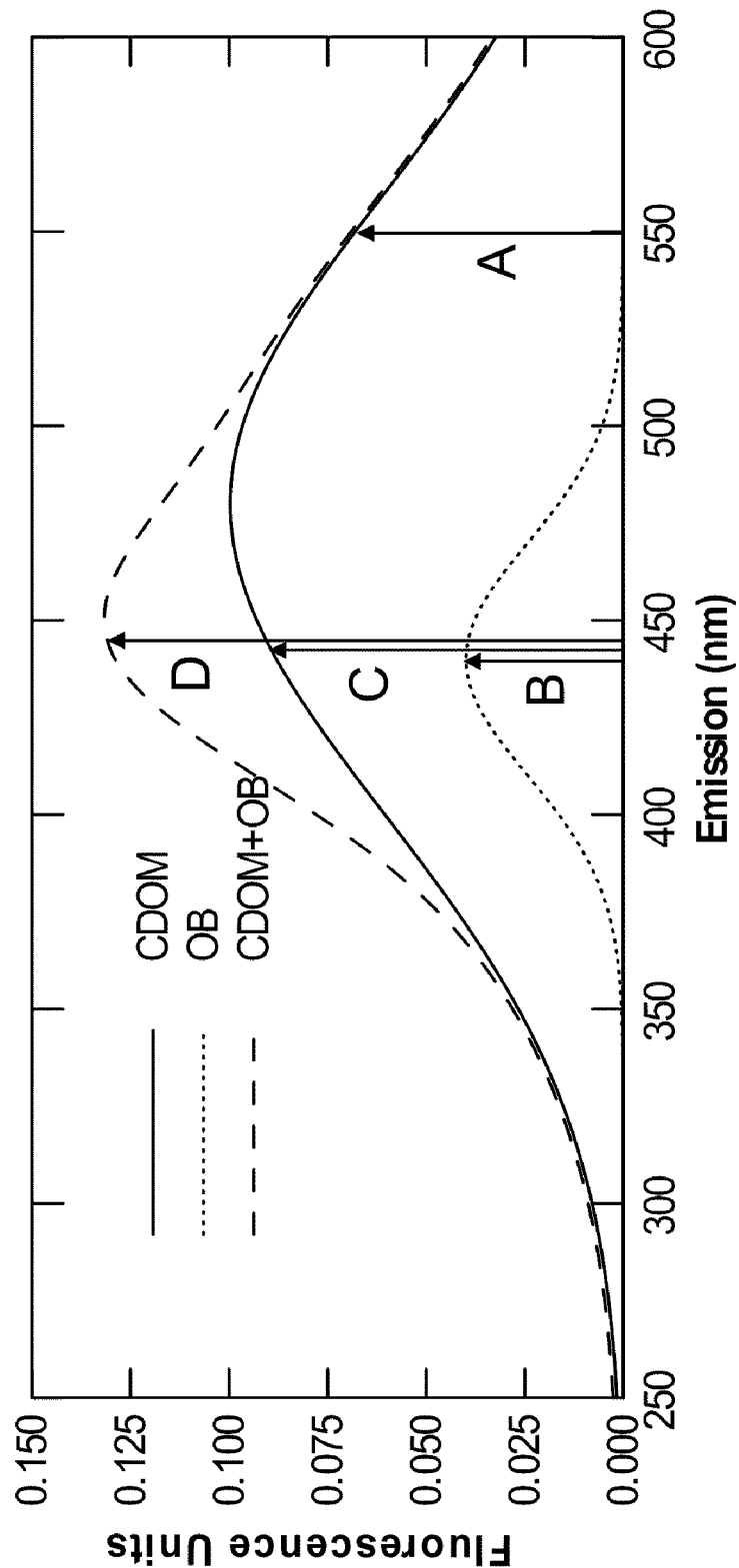
FIG. 2 is a graph illustrating OB and CDOM levels in a water sample.

FIG. 2 illustrates a full spectrum fluorescence emission obtained using 350 nm excitation of a typical water sample. The spectral data points are corrected for absorption as discussed in more detail below. In order of increasing peak height, the spectra show emission for laboratory pure water containing only a given amount of OB, for a collected water sample containing CDOM alone and for the same collected water sample spiked with the same OB amount as is in the laboratory pure water (OB+CDOM). In FIG. 2, arrows A and C respectively indicate CDOM fluorescence at 550 and 440 nm, arrow B indicates OB fluorescence at 440 nm, and arrow D indicates fluorescence contributed by OB+CDOM at 440 nm. Arrows B, C and D have been offset slightly for clarity. Arrow B corresponds to a maximum in the OB fluorescence signal. Arrows C and A correspond to a relatively broad peak in the CDOM fluorescence signal from about 440 to 550 nm.

Quantitative OB measurements may be obtained using a variety of signal processing procedures illustrated in more detail below, it being understood that similar results may be accomplished using standard manipulations to provide different but equivalent end results. In one exemplary signal processing embodiment, the expected fluorescence from CDOM alone, based on collected data or regionally specific measurements from an area in which OBs are assumed to be absent, is calculated. The ratio between absorption corrected fluorescence, $F_{440}/F_{550}$, in a 'clean' area is used to calculate the expected $F_{440}$ due to CDOM alone from all observed $F_{550}$. A 'clean' area is identified as an area in which there is no expected wastewater effluent or where the $F_{440}/F_{550}$ ratio has the lowest ratio observed for a specific field survey. The $F_{440Clean}/F_{550Clean}$ ratio can be termed a survey constant (SC) and may be used to process all data collected for a given survey in a geographic region. Using this method, the $F_{440Clean}/F_{550Clean}$ ratio from a clean area (e.g., the lowest observed C/A value for sample spectral data collected and illustrated as in FIG. 2) is used to calculate the expected CDOM $F_{440}$ values (e.g., C in FIG. 2) from all observed $F_{550}$ values (e.g., A in FIG. 2) for a given sample set. The observed $F_{440}$ values (e.g., C+D in FIG. 2) are reduced by the expected CDOM alone $F_{440}$ values (e.g., C in FIG. 2) and the calculated OB Fog quantities (e.g., D-C in FIG. 2) will be linear with respect to OB level without regard to background CDOM fluorescence. The fluorescence due to OBs alone in a given observed water sample ($F_{OB}$) can be determined using the following formulas I and II in which fluorescence data, $F_{440}$, $F_{550}$, $F_{440Clean}$, and $F_{550Clean}$ have all been absorption corrected:

$$SC = F_{440Clean}/F_{550Clean} \qquad \text{I}$$

$$F_{OB} = F_{440} - SC \cdot F_{550} \qquad \text{II}$$

The computed $(F_{440Clean}/F_{550Clean}) \cdot F_{550}$ quantity, or the computed $SC \cdot F_{550}$ quantity, is that portion of the $F_{440}$ which is due to CDOM alone. The fluorescence due to OB present is computed as the difference between the observed and the expected $F_{440}$.

Additional equations and variables may be employed to make the recited absorption corrections. When measuring fluorescence in water samples, increased sample absorption will reduce the observed fluorescence in a phenomenon known as the inner filter effect, in which the excitation energy reaching the sample is reduced and the fluorescence emission energy is also absorbed and reduced. Most absorption in ambient waters is due to CDOM and is proportional to the CDOM concentration. When CDOM varies in concentration and absorption, the resulting raw fluorescence response also varies. The raw collected fluorescence data should accordingly be corrected for absorption by CDOM components. Absorption coefficients and the corresponding absorption correction factors may be obtained using data determined through direct measurements at some or all of the employed wavelengths, e.g., at the midpoints or throughout the wavelength ranges employed for excitation and the first and second emission regions. Such direct measurements may be obtained in a variety of ways, e.g., by equipping the one or more fluorometers with suitable absorption measuring sensors or by using a further instrument to measure sample absorption. The direct measurement results so obtained may provide absorption coefficients and absorption correction factors for the specific fluorometer employed, and to the same or a lesser extent may provide absorption coefficients and absorption correction factors for other fluorometers of the same or similar design. If desired, absorption may be measured at a single wavelength (e.g., 550 nm) and CDOM absorption at other wavelengths modeled using for example equations adapted from A. Bricaud, A. Morel and L. Prieur, *Absorption by dissolved organic matter of the sea (yellow substance) in the UV and visible domains*, Limnology & Oceanography 26:43-53 (1981). Fluorometer-specific empirical relationships of absorption at one wavelength with fluorescence at a given wavelength or wavelength region may also be used to model absorption data at one wavelength, and equations used to model the remaining absorption coefficients and absorption correction factors. Discrete samples collected during fieldwork may also be processed for absorption data and used to refine default relationships of absorption coefficients with fluorescence and absorption correction factors during data post-processing. The absorption correction factors may thus be based on either measured or modeled absorptive properties of a waterway. CDOM absorptive properties may be measured using optical density data obtained, for example using a spectrophotometer. Using the excitation and fluorescence detection wavelengths mentioned above, an absorption coefficient $a_{350}$ may be computed at 350 nm (the midpoint of the 300-400 nm excitation range), and absorption coefficients $a_{440}$ and $a_{550}$ may be computed at 440 nm and 550 nm (the preferred first and second emission wavelengths). These absorption coefficients may be conveniently be computed from optical density (OD, also known as absorbance) or % transmission (% T) measurements determined from the incident radiation on a sample ($Io\lambda$) and the amount of radiation remaining after transmission through the sample ($I\lambda$) along a given pathlength (L, in meters) where radiation is centered at the wavelength of interest ($\lambda$), using for example the following relationships:

$$OD\lambda = -\log_{10}(I\lambda/Io\lambda) \qquad \text{IIa}$$

$$\text{or } \%T\lambda = 100*(I\lambda/Io\lambda) \qquad \text{IIIb}$$

$$a\lambda = 2.303 * OD\lambda/L \qquad \text{IVa}$$

$$\text{or } a\lambda = 2.303*(-1)*\log_{10}(\% T\lambda/100)/L \qquad \text{IVb}$$

The associated absorption correction factors ($CF_{350/440}$, $CF_{350/550}$) may then be computed to correct the raw fluorescence data for the inner filter effect (reduced fluorescence) produced by the absorption of both excitation and emission energies during passage through the fluorometer sample cell. The absorption correction factors are specific for excitation and emission wavelength pairs and may be computed by adapting equations shown in Lakowicz, J., *Principles of Fluorescence Spectroscopy*, 3rd ed. pp 55-57 (2006) as follows:

$$CFex/em = 10^{((aex+aem)*(p/2)/2.303)} \qquad \text{V}$$

where:
ex=midpoint of the excitation wavelength range,
em=midpoint of the emission wavelength range,
p=the size of the fluorescence sample cell, in meters, and
aex, aem=absorption coefficients at the excitation and emission wavelengths.

Although optical density measurements may be determined at many different wavelengths, absorption coefficients of CDOM components in water samples may be determined from optical density measurements at a wavelength of 550 nm, for example, and used to extrapolate or model absorption at alternate wavelengths, for example, 440 nm, by adapting relationships identified in Jerlov, N. G., *Marine Optics*, p. 56 (1976) and equations described in Bricaud et al., supra, as follows:

$$a\lambda = a_{550}*e^{-S(\lambda - 550)} \qquad \text{V}$$

where S is the spectral slope.

The spectral slope parameter, S, varies with age of CDOM, but is relatively stable for a given region. A default value of 0.015 may be employed during an initial field survey, and geographically-specific values may be determined from discrete samples and applied during post-processing.

Absorption coefficients of CDOM components in water samples may also be modeled from site- and fluorometer-specific relationships of absorption with fluorescence emission at a wavelength of 550 nm, for example, or fluorescence at other wavelengths where CDOM is the dominant fluorophore. Instrument-specific absorption:fluorescence relationships are usually relatively robust and default values may be used until site-specific relationships can be developed. Relationships of raw fluorescence (RF) with absorption are curvilinear as absorption corrections have not been applied and take the form:

$$a550 = A*RF_{550} + B*RF_{550}^2 + C \qquad \text{VII}$$

where A, B and C are constants for a given survey. Revisions to site-specific absorption:fluorescence measurements may be applied during post-processing. Absorption at other needed wavelengths may then be estimated by adapting the equations of Bricaud et al., supra.

After modeled or measured absorption coefficients have been determined for the desired fluorescence excitation and emission wavelengths, absorption correction factors may be determined as discussed above. Corrected fluorescence data, $F_{440}$, $F_{550}$ may then be computed as raw fluorescence data (RF) times the appropriate absorption correction factor, CF, or:

$$F\lambda = CF_{350/\lambda} * RF\lambda \qquad \text{VIII}$$

Using the preferred excitation and emission wavelengths discussed above, the quantitative OB amount in a water sample may be determined as follows:

$$SC = (CF_{Clean350/440} * F_{440Clean}) / (CF_{Clean350/550} * F_{550Clean}) \qquad \text{IX}$$

$$FOB = CF_{350/440} * RF_{440} - SC * CF_{350/550} * RF_{550} \qquad \text{X}$$

where:
RF=raw fluorescence
CF=ex/em specific absorption correction factor
SC=the survey constant, SC, computed from a sample or location where OB is absent or may be considered to be absent.

While the identified 'clean' ratios or survey constant SC may remain constant for each survey, the remaining correction factors desirably are computed for each sample observation. The survey constants may be revised during post-processing if a lower clean ratio is subsequently identified.

The calculated OB amounts may also be used to make quantitative estimates of detergent levels. For example, standardization of calculated OB levels to the concentration of detergent may be accomplished by linear regression of the computed OB fluorescence with known standard detergent concentrations.

Further details regarding the calculations discussed above may be found in Dixon, L. K., *Tracing anthropogenic wastes: Detection of Optical Brighteners in a gradient of natural organic matter fluorescence*, Ph.D. Dissertation, University of South Florida (Approved Nov. 9, 2009) and in Dixon, L. K., *Optical Brighteners: PARAFAC analyses of EEM fluorescence data for the conceptual design of field instrumentation and methods. Final Report*, Mote Marine Laboratory Technical Report No. 1316 (Feb. 16, 2009), the disclosures of which are incorporated herein by reference.

Figure 3:
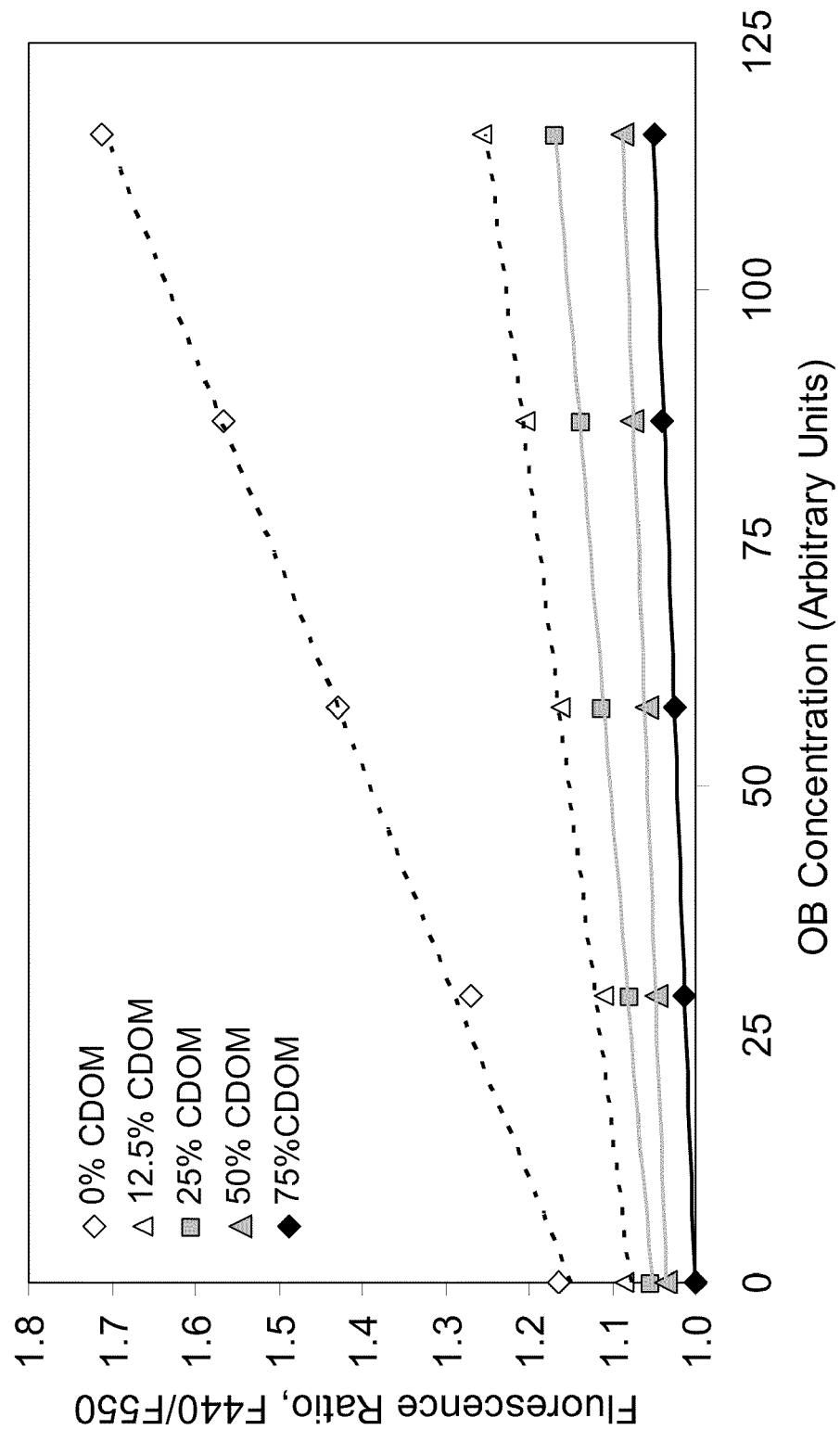
FIG. 3 is a graph showing fluorescent OB response as the ratio $F_{440}/F_{550}$ in waters of varying CDOM concentration.

FIG. 3 illustrates the measurement of OB fluorescence using previously-reported techniques, see L. K. Dixon and P. Julian, *Phillippi Creek Optical Brightener Investigation for Sarasota County Water Resources*, Mote Marine Laboratory Technical Report No. 1038 (2005) and L. Dixon, H. Taylor, E. Staugler and J. Scudera, *Development of a fluorescent method to detect optical brighteners in the presence of varying concentrations of fluorescent humic substances: Identifying regions influenced by OSTDS in the estuarine waters of Charlotte Harbor*, Mote Marine Laboratory Technical Report No. 1045 (2005). These techniques employed simple $F_{440}/F_{550}$ fluorescence ratios to indicate OB presence and in some instances applied various absorption corrections, temperature corrections or instrumental gain adjustments. In FIG. 3, CDOM-containing seawater samples were spiked with various levels of OBs and evaluated to determine $F_{440}/F_{550}$ for waters containing 0, 12.5, 25, 50 and 75 vol. % high CDOM water in seawater. For a given CDOM level, the ratio of fluorescence due to CDOM alone at 440 nm compared to 550 nm ($F_{440}/F_{550}$, or C:A in FIG. 1) remained relatively constant across a range of OB concentrations. However, as shown by the variety of curves in FIG. 3, the ratio $F_{440}/F_{550}$ varied as the CDOM level varied. As CDOM concentration and fluorescence at both 440 nm and 550 nm vary, the portion of the ratio due to fluorescence from a given amount of OB will vary inversely. At high CDOM concentrations, a given amount of OB will increase the ratio signal very slightly, while at low CDOM concentrations, the ratio will be increased a much larger amount over waters with CDOM alone. As a result, the response of the ratio signal to OB is non-quantitative over the range of ambient CDOM concentrations typically observed, and higher CDOM concentrations can actually be interpreted as reduced OB concentrations.

Figure 4:
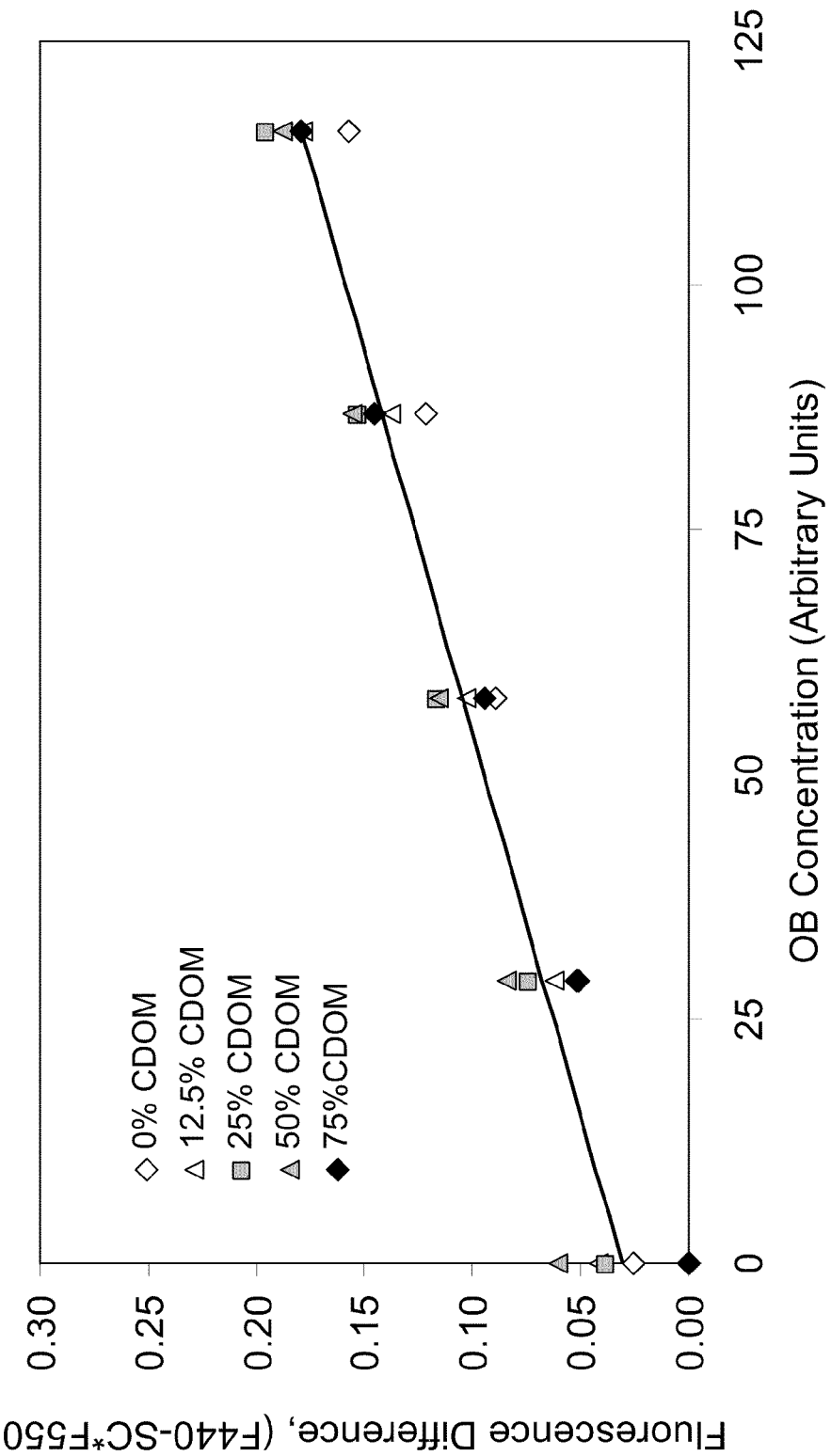
FIG. 4 is a graph showing fluorescent OB response in waters of varying CDOM concentration measured according to the present invention.

FIG. 4 shows the results obtained when the FIG. 3 samples were analyzed according to the present invention. The observed and expected fluorescence at 440 nm responded linearly to OB concentration, without regard to the amount of CDOM present. There were no statistically significant differences between the slopes of the individual CDOM:seawater preparations and so only one line is illustrated.

The disclosed apparatus and method may also employ instrumental gain adjustments to show variations in CDOM concentration. For example, in an area with high CDOM (manifested for example by a high raw $F_{550}$ value) where OBs are absent or may be assumed to be absent, then the instrument gain for both $F_{440}$ and $F_{550}$ may be set to a non-zero value, for example, to 5.00 on a 10 point scale. Subsequent $F_{440}$ fluorescence emission readings that are greater than the observed $F_{550}$ value can be assumed to indicate the presence of OBs. Instrumental gains would remain the same for each survey. Variations observed in $F_{550}$ would be indicative of varying CDOM concentrations. The approach differs from work such as that in Dixon and Julian, supra, in that the OB amount will generally correspond to the difference between the two gain adjusted fluorescence values rather than the ratio of the two values. The gain adjusted, absorption corrected 550 nm signal for subsequent samples desirably is subtracted from the gain adjusted, absorption corrected 440 nm fluorescence. The resulting quantity is due to OB fluorescence and has the same fluorescent response to a given amount of OB regardless of CDOM concentration. After presumptive areas for human contamination are identified by high fluorescence due to OB, these areas may be re-sampled for more detailed water analysis.

In another embodiment, the fluorometer or fluorometers are first standardized against known standards, such as a specified concentration of quinine sulfate. Subsequent fluorescence measurements taken at multiple wavelengths may be followed by signal processing such as that described above. Use of such standards may improve comparability between work conducted by different entities or on different days, by standardizing the fluorometric response to a given amount of OB.

Various modifications and alterations of this invention will be apparent to those skilled in the art without departing from this invention. This invention should not be restricted to that which has been set forth herein only for illustrative purposes.

The invention claimed is:

1. An apparatus for quantitatively measuring the amount of optical brighteners in a selected water sample, the apparatus comprising:
  a. a chamber where the selected sample is exposed to ultraviolet excitation at a wavelength of about 300 to 400 nm;
  b. one or more fluorometers that measure raw fluorescence emission from the selected sample at a first emission wavelength of about 400 to 500 nm and at a second emission wavelength of about 500 to 600 nm;
  c. one or more electronic computational devices that:
    i. correct raw fluorescence emission measurements from the selected sample for sample absorption at the excitation wavelength and first and second emission wavelengths using measured, modeled or both measured and modeled absorption coefficients to provide absorption-corrected fluorescence emission values for the selected sample at the first and second emission wavelengths;
    ii. determine the ratio of the absorption-corrected fluorescence emission value at the first emission wavelength to the absorption-corrected fluorescence emission value at the second emission wavelength for a comparison water sample in which optical brighteners are not present or are only minimally present;
    iii. use such ratio and the absorption-corrected fluorescence emission value for the selected sample at the second emission wavelength to determine the expected or background absorption-corrected fluorescence emission value for the selected sample at the first emission wavelength; and
    iv. determine the amount of optical brighteners in the selected sample by subtracting the expected or background absorption-corrected fluorescence emission value for the selected sample at the first emission wavelength from the absorption-corrected fluorescence emission value for the selected sample at the first emission wavelength.

2. An apparatus according to claim 1 wherein two or more fluorometers arranged in a parallel flow circuit measure raw fluorescence emission at the first and second emission wavelengths.

3. An apparatus according to claim 1 wherein two or more fluorometers arranged in a series flow circuit measure raw fluorescence emission at the first and second emission wavelengths.

4. An apparatus according to claim 1 wherein a single fluorometer measures raw fluorescence emission at the first and second emission wavelengths.

5. An apparatus according to claim 1 wherein the one or more fluorometers or a further instrument measure sample absorption.

6. An apparatus according to claim 1 wherein the first emission wavelength is about 440 nm and the second emission wavelength is about 550 nm.

7. An apparatus according to claim 1 wherein the one or more fluorometers measure raw fluorescence emission by flowing water sample through a continuous flow-through circuit.

8. An apparatus according to claim 1 wherein the one or more fluorometers measure raw fluorescence emission in collected discrete water samples.

9. An apparatus according to claim 1 further comprising a display that provides quantitative optical brightener information corrected for sample absorption and chromophoric dissolved organic matter levels.

10. An apparatus according to claim 1 further comprising a display that provides quantitative chromophoric dissolved organic matter information.

11. A method for quantitative measurement of the amount of optical brighteners in a selected water sample, which method comprises:
   a. exposing such selected sample to ultraviolet excitation at a wavelength of about 300 to 400 nm;
   b. measuring raw fluorescence emission from the selected sample at a first emission wavelength of about 400 to 500 nm and at a second emission wavelength of about 500 to 600 nm;
   c. correcting raw fluorescence emission measurements from the selected sample for sample absorption at the excitation wavelength and first and second emission wavelengths using measured, modeled or both measured and modeled absorption coefficients to provide absorption-corrected fluorescence emission values for the selected sample at the first and second emission wavelengths;
   d. determining the ratio of the absorption-corrected fluorescence emission value at the first emission wavelength to the absorption-corrected fluorescence emission value at the second emission wavelength for a comparison water sample in which optical brighteners are not present or are only minimally present;
   e. using such ratio and the absorption-corrected fluorescence emission value for the selected sample at the second emission wavelength to determine the expected or background absorption-corrected fluorescence emission value for the selected sample at the first emission wavelength; and
   f. determining the amount of optical brighteners in the selected sample by subtracting the expected or background absorption-corrected fluorescence emission value for the selected sample at the first emission wavelength from the absorption-corrected fluorescence emission value for the selected sample at the first emission wavelength.

12. A method according to claim 11 wherein the first emission wavelength is about 440 nm and the second emission wavelength is about 550 nm.

13. A method according to claim 11 comprising measuring water samples while on a waterway by flowing such samples through a continuous flow-through circuit.

14. A method according to claim 11 comprising measuring water samples while on a waterway or in a laboratory by collecting a plurality of discrete water samples.

15. A method according to claim 11 further comprising measuring sample absorption using the one or more fluorometers or a further instrument.

16. A method according to claim 11 comprising correcting the first emission wavelength and second emission wavelength raw measurements for sample absorption using measured absorption coefficients.

17. A method according to claim 11 comprising correcting the first emission wavelength and second emission wavelength raw measurements for sample absorption using modeled absorption coefficients.

18. A method according to claim 11 further comprising displaying quantitative optical brightener information corrected for sample absorption and chromophoric dissolved organic matter levels.

19. A method according to claim 11 further comprising displaying quantitative chromophoric dissolved organic matter information.

20. A method according to claim 11 further comprising adjusting instrumental gain to a non-zero value using a sample with high chromophoric dissolved organic matter content and low or no optical brightener content, and subtracting a gain adjusted, absorption corrected 550 nm signal from a gain adjusted, absorption corrected 440 nm fluorescence signal to provide information concerning optical brightener content and variations in chromophoric dissolved organic matter content in subsequent samples.

* * * * *